US00PP29090P2

(12) United States Plant Patent
Zaiger et al.

(10) Patent No.: US PP29,090 P2
(45) Date of Patent: Mar. 13, 2018

(54) CHERRY TREE NAMED 'ROYAL SONIA'

(50) Latin Name: *Prunus avium*
Varietal Denomination: Royal Sonia

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 15/330,726

(22) Filed: Nov. 1, 2016

(51) Int. Cl.
*A01H 5/08* (2006.01)

(52) U.S. Cl.
USPC ..... Plt./181

(58) Field of Classification Search
USPC ..... Plt./181
CPC .... A01H 5/085; A01H 5/0216; A01H 5/0837; A01H 5/08
See application file for complete search history.

*Primary Examiner* — June Hwu

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Regular and productive bearer of medium to large size fruit.
3. Fruit with an attractive red skin color.
4. Fruit with very good flavor and eating quality with a good balance between acid and sugar.
5. Fruit with firm flesh that has good handling and shipping qualities.

1 Drawing Sheet

Botanical designation: *Prunus avium.*
Variety denomination: 'Royal Sonia'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Lynn' Cherry (U.S. Plant Pat. No. 19,589) and 'Royal Hazel' Cherry (U.S. Plant Pat. No. 19,920).

STATEMENT REGARDING FEDERALLY SPONSORED RESEARCH AND DEVELOPMENT

Not applicable.

ORIGIN OF THE VARIETY

The present new variety of cherry tree (*Prunus avium*) was originated by us in our experimental orchard located near Modesto, Calif., as an open pollinated seedling from 'Royal Hazel' Cherry (U.S. Plant Pat. No. 19,920). A large number of these open pollinated seedlings were budded and maintained on established 'Mahaleb' Rootstock (non-patented) to accelerate fruit production for evaluation. Under close and careful observation the present seedling exhibited desirable fruit and tree characteristics and was selected in 2005 for additional asexual reproduction and commercialization.

ASEXUAL REPRODUCTION OF THE VARIETY

In 2005, asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree (*Prunus avium*) is of large size, vigorous, upright growth and a regular and productive bearer of medium to large size fruit with attractive red skin color. The fruit is further characterized by having very good flavor and eating quality with good handling and shipping qualities. In comparison to its seed parent 'Royal Hazel' Cherry (U.S. Plant Pat. No. 19,920) the flowers of the new variety are self-compatibility compared to self-sterile and the fruit of the new variety is approximately 7 days later in maturity. In comparison to the commercial variety 'Royal Lynn' Cherry (U.S. Plant Pat. No. 19,589) the fruit of the new variety is approximately 2 weeks later in maturity.

DESCRIPTION OF THE PHOTOGRAPH

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 11 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 11 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive. Produces adequate fruit set annually.

*Bearer*.—Regular, has had adequate fruit set 9 consecutive years. No alternate bearing observed.

*Fertility*.—Self fertile. Sets fruit under the bag.

*Density*.—Medium dense, usually pruned to vase shape to increase amount of sunlight to center of tree to enhance fruit color, Brix and health of fruit spurs.

*Hardiness*.—Hardy in all stone fruit growing areas of California. Tree grown in USDA Hardiness Zone 9. Winter chilling requirement approximately 650 hours at or below 45° F.

Trunk:

*Size*.—Large. Average circumference 45.7 cm at 27.9 cm above ground on a 11 year old tree.

*Stocky*.—Medium stocky.

*Texture*.—Medium shaggy, roughness increases with age.

*Color*.—Varies from 10YR 5/2 to 10YR 3/2.

Branches:

*Size*.—Medium. Average circumference 17.0 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 35 in a 25.8 square cm section. Average length 4.5 mm. Average width 1.9 mm. Color varies from 5YR 5/10 to 7.5YR 5/10.

*Color*.—New growth varies from 2.5GY 6/8 to 5GY 6/8. Mature growth varies from 5YR 2/2 to 7.5YR 3/2, varies with age of growth.

Leaves:

*Size*.—Medium to large. Average length 149.5 mm. Average width 65.0 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 37.2 mm. Average width 1.8 mm. Longitudinally grooved. Surface — pubescent. Color varies from 5GY 6/6 to 5R 3/4.

*Glands*.—Type — reniform. Size — large. Average length 2.5 mm. Average diameter 1.7 mm. Average number 2, varies from 1 to 3. Located primarily on the upper portion of the petiole and the base of the leaf blade. Color varies from 5R 3/8 to 7.5R 3/8.

*Stipules*.—Average number 2. Average length 11.7 mm. Edges — pectinate. Color varies from 5GY 6/6 to 2.5R 4/4.

*Color*.—Upper surface varies from 5GY 3/6 to 7.5GY 3/6. Lower surface varies from 5GY 4/4 to 7.5GY 4/4. Midvein color varies from 2.5GY 6/6 to 5GY 7/6.

Flower buds:

*Size*.—Medium to large. Average length 16.8 mm. Average diameter 8.9 mm.

*Hardiness*.—Hardy with respect to California winters.

*Density*.—Very dense.

*Form*.—Conical, becoming elongated just before opening.

*Pedicel*.—Average length 13.5 mm. Average width 1.1 mm. Color varies from 5GY 5/8 to 5GY 5/6. Surface — glabrous.

*Color*.—N 9.5/(white).

*Number of buds per spur*.—Average number 8, varies from 5 to 14.

Flowers:

*Blooming period*.—Date of First Bloom Feb. 28, 2016. Date of Petal Fall Mar. 9, 2016, varies slightly with climatic conditions.

*Size*.—Medium to large. Average height 18.2 mm. Average diameter 33.3 mm.

*Petals*.—Number — normally 5, alternately arranged to sepals. Size — medium to large. Average length 16.2 mm. Average width 13.8 mm. Form — ovate to orbicular. Arrangement — overlapping to free. Petal apex rounded. Petal base — rounded to somewhat truncate. Margin — entire. Color N 9.5/(white). Both upper and lower surface glabrous.

*Sepals*.—Number — normally 5, alternately arranged to sepals. Size — large. Average length 8.5 mm. Average width 5.4 mm. Shape — triangular. Apex — rounded to triangular. Margin — entire. Both upper and lower surfaces glabrous. Color — upper surface varies from 5GY 5/6 to 5GY 4/6. Lower surface varies from 5GY 4/8 to 5R 3/4.

*Stamens*.—Average number per flower 34. Average filament length 13.1 mm. On average, the stamens are below the height of the petals. Filament color N 9.5/(white). Anther color varies from 2.5Y 7/10 to 5Y 7/10.

*Pollen*.—Self fertile, sets fruit under the bag. Color varies from 2.5Y 7/10 to 2.5Y 6/10.

*Pistil*.—Normally 1. Average length 17.3 mm. Position of stigma an average of 1.2 mm above the anthers. Surface — glabrous. Color varies from 2.5GY 7/6 to 2.5GY 7/8.

*Fragrance*.—Heavy.

*Flower color: N* 9.5/(white).

*Pedicel*.—Large. Average length 15.3 mm. Average width 1.3 mm. Color varies from 2.5GY 5/8 to 5GY 5/6.

*Number flowers per flower bud*.—Average 5, varies from 3 to 5.

Fruit:

*Maturity when described*.—Firm ripe and ready for consumption.

*Date of first picking*.—May 16, 2016.

*Date of last picking*.—May 26, 2016, varies slightly with climatic conditions.

*Size*.—Medium to large. Average diameter axially 26.8 mm. Average transversely in suture plane 24.8 mm. Average weight 5.7 grams, varies slightly with fertility of the soil, amount of thinning and climatic conditions.

*Form*.—Globose.

*Suture*.—Nearly smooth.

*Ventral surface*.—Smooth.

*Apex*.—Rounded.

*Base*.—Slightly retuse.

*Stem cavity*.—Rounded. Average depth 2.7 mm. Average breadth 3.5 mm.

Stem:

*Size*.—Medium. Average length 36.5 mm. Average diameter 1.5 mm.

*Color*.—Varies from 2.5GY 5/6 to 5GY 5/8.

Flesh:

*Ripens*.—Evenly.

*Texture*.—Firm, meaty.

*Fibers*.—Few, small, tender.

*Firmness*.—Firm, comparable to other commercial cherry varieties.

*Aroma*.—Slight.

*Amydgalin*.—Undetected.

*Eating quality*.—Very good.

*Flavor*.—Very good, good balance between acid and sugar.

*Juice*.—Heavy amount, enhances flavor.

*Acidity*.—Not available.

*Brix*.—Average Brix 18.4°, varies slightly with amount of fruit per tree and climatic conditions.

*Color*.—Varies from 5R 3/8 to 5R 3/10.

*Pit cavity*.—Average length 13.5 mm. Average width 10.9 mm. Average depth 4.0 mm. Color 7.5R 2/6.

Skin:

*Thickness*.—Medium.

*Surface*.—Smooth.

*Bloom*.—Wanting.

*Tendency to crack*.—None during dry weather, only slight tendency to crack in wet weather. Depends on stage of maturity.

*Color*.—Varies from 5R 3/10 to 7.5R 2/8.

*Tenacity*.—Tenacious to flesh.

*Astringency*.—Undetected.

Stone:

*Type*.—Clingstone, medium adherence to flesh.

*Size*.—Medium. Average length 13.0 mm. Average width 10.4 mm. Average thickness 7.4 mm.

*Form*.—Ovoid.

*Base*.—Flat.

*Apex*.—Slight point. Average length 0.4 mm.

*Surface*.—Very slightly pitted throughout. Small ridges run along each side of the suture line from base to apex.

*Sides*.—Varies from equal to unequal with one side extending further from the suture plane.

*Ridges*.—Relatively smooth, a small, narrow ridge on each side of suture extending from base toward apex.

*Tendency to split*.—None.

*Color*.—Varies from 10YR 7/6 to 10YR 6/6 when dry.

Kernel:

*Size*.—Small to medium. Average length 9.3 mm. Average width 5.9 mm. Average depth 3.8 mm.

*Form*.—Ovoid.

*Viability*.—Viable, complete embryo development.

*Skin color*.—Varies from 5Y 9/2 to 2.5Y 9/4.

Use:

*Dessert: Market — local and long distance.*

Keeping quality: Good, held firm in cold storage for 2 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of cherry tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree (*Prunus avium*), substantially as illustrated and described.

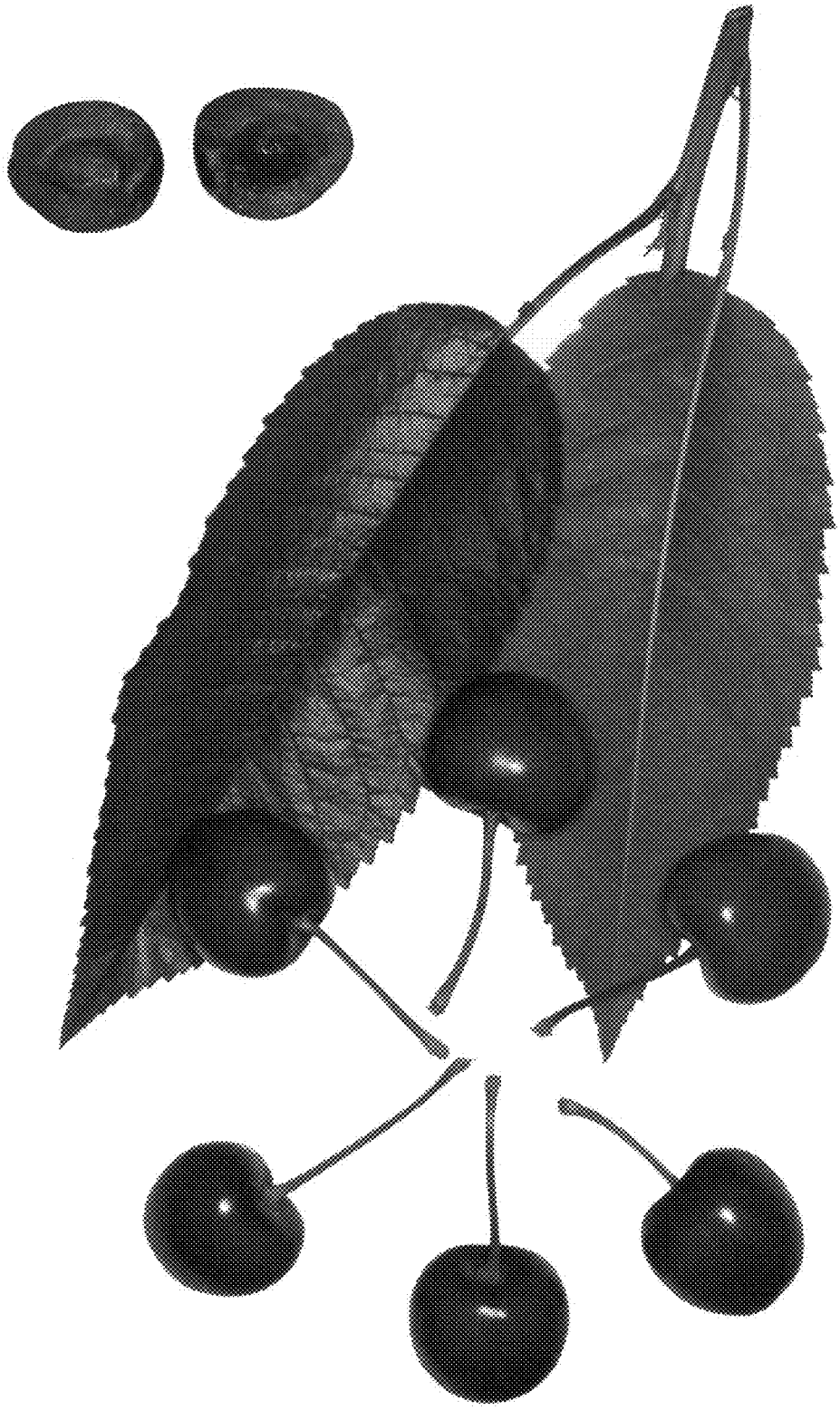

* * * * *